(12) United States Patent
Gupta (10) Patent No.: US 10,507,123 B2
(45) Date of Patent: Dec. 17, 2019

(54) SELF-EXPANDABLE SCAFFOLDING DEVICE FOR THE TREATMENT OF ANEURYSMS

(71) Applicant: Monarch Biosciences, Inc., Los Angeles, CA (US)

(72) Inventor: Vikas Gupta, Los Angeles, CA (US)

(73) Assignee: MONARCH BIOSCIENCES, INC., Los Angeles, CA (US)

( * ) Notice: Subject to any disclaimer, the term of this patent is extended or adjusted under 35 U.S.C. 154(b) by 125 days.

(21) Appl. No.: 15/655,674

(22) Filed: Jul. 20, 2017

(65) Prior Publication Data

US 2017/0348119 A1 Dec. 7, 2017

Related U.S. Application Data

(63) Continuation of application No. PCT/US2016/014191, filed on Jan. 20, 2016.

(60) Provisional application No. 62/105,432, filed on Jan. 20, 2015.

(51) Int. Cl.
*A61F 2/852* (2013.01)
*A61F 2/92* (2013.01)
(Continued)

(52) U.S. Cl.
CPC ............... *A61F 2/852* (2013.01); *A61F 2/91* (2013.01); *A61F 2/92* (2013.01);
(Continued)

(58) Field of Classification Search
CPC ..... A61F 2/852; A61F 2/91; A61F 2/92; A61F 2002/825; A61F 2210/0076;
(Continued)

(56) References Cited

U.S. PATENT DOCUMENTS 4,877,030 A 10/1989 Beck et al.
5,007,926 A 4/1991 Derbyshire
(Continued)

FOREIGN PATENT DOCUMENTS

WO WO2013/191005 A1 12/2013

OTHER PUBLICATIONS

PCT International Search Report and Written Opinion of International Application No. PCT/US2016/014191, 8 pages, dated Mar. 29, 2016.
(Continued)

*Primary Examiner* — Paul B Prebilic
(74) *Attorney, Agent, or Firm* — Haynes and Boone LLP (57) ABSTRACT

A stent includes a first longitudinally extended cylinder having a C-shaped cross-section and a second longitudinally extended cylinder having a C-shaped cross-section. The first cylinder includes a plurality of first longitudinal struts and an array of first radial struts extending between the first longitudinal struts. The second cylinder includes a plurality of second longitudinal struts and an array of second radial struts extending between the second longitudinal struts. The first cylinder and the second cylinder are configured to form a dense mesh structure when assembled. When assembled, the second cylinder may be disposed in the first cylinder. The first cylinder may overlap with the second cylinder to form the dense mesh structure.

12 Claims, 13 Drawing Sheets

(51) Int. Cl.
*A61F 2/91* (2013.01)
*A61F 2/82* (2013.01)

(52) U.S. Cl.
CPC ... *A61F 2002/823* (2013.01); *A61F 2002/825* (2013.01); *A61F 2210/0014* (2013.01); *A61F 2220/0058* (2013.01); *A61F 2220/0075* (2013.01); *A61F 2230/0013* (2013.01); *A61F 2250/0017* (2013.01); *A61F 2250/0098* (2013.01)

(58) Field of Classification Search
CPC ........ A61F 2220/0058; A61F 2250/006; A61F 2230/0013; A61F 2250/0063; A61F 2250/0065; A61F 2250/001
See application file for complete search history.

(56) References Cited

U.S. PATENT DOCUMENTS

| | | | |
|---|---|---|---|
| 5,735,871 A * | 4/1998 | Sgro | A61F 2/82 606/194 |
| 7,815,674 B1 | 10/2010 | Ragazzo | |
| 2002/0052648 A1 | 5/2002 | McGuckin, Jr. et al. | |
| 2002/0173839 A1 * | 11/2002 | Leopold | A61B 17/12118 623/1.15 |
| 2007/0239261 A1 | 10/2007 | Bose et al. | |
| 2008/0140172 A1 | 6/2008 | Carpenter et al. | |
| 2009/0105806 A1 | 4/2009 | Benjamin et al. | |
| 2009/0210049 A1 * | 8/2009 | Thielen | A61F 2/91 623/1.16 |
| 2010/0262216 A1 | 10/2010 | Xue | |
| 2011/0276125 A1 * | 11/2011 | Walker | A61F 2/915 623/1.15 |
| 2013/0204343 A1 | 8/2013 | Shalev | |
| 2014/0163664 A1 * | 6/2014 | Goldsmith | A61B 17/00491 623/1.11 |
| 2014/0180377 A1 | 6/2014 | Bose et al. | |
| 2016/0067071 A1 * | 3/2016 | Jose | A61L 31/005 623/1.15 |

OTHER PUBLICATIONS

Extended European Search Report dated Dec. 17, 2018; Application No. 16 74 0711.3; 10 pages.

* cited by examiner

SELF-EXPANDABLE SCAFFOLDING DEVICE FOR THE TREATMENT OF ANEURYSMS

CROSS-REFERENCES TO RELATED APPLICATIONS

This application is a continuation of International Application No. PCT/US2016/014191, filed Jan. 20, 2016, which claims the benefit of U.S. Provisional Application No. 62/105,432, filed Jan. 20, 2015, the contents of all of which are hereby incorporated by reference in their entirety.

TECHNICAL FIELD

This invention relates to endovascular devices such as stents for the treatment of tissue defects such as aneurysms.

BACKGROUND

Tissue defects involve an absence of healthy tissue in a body area where such tissue would normally be present. For example, a common tissue defect includes aneurysms, in which there is a defect in a blood vessel wall that causes an outpouching of the vessel tissue. Aneurysm may form in disparate locations such as the aorta, iliac arteries, renal arteries, popliteal arteries, splenic arteries, femoral arteries, tibial arteries, and throughout the neurovasculature. Other common tissue defects include arteriovenous fistulas, intestinal fistulas, colonic fistulas, anal fistulas, hernias and traumatic wounds. Aneurysms and other tissue defects may be treated using surgical methods, such as clipping, or endovascular methods, such as flow diversion techniques using a flow diverter (e.g., a covered stent) or coil embolization techniques using coils or a combination of coils and a stent.

In coil embolization techniques, small metallic coils are delivered to the sac of an aneurysm. The coils pack the sac densely to limit blood flow in the sac, thereby inducing clotting of the blood inside the sac and, eventually, healing of the aneurysm. However, such coil embolization techniques can be used only with aneurysms with a narrow neck region to hold the coil in place. Further, such coil embolization techniques suffer from complications, including the risk of recanalization in which blood flow returns to the sac and further swells the sac.

Figure 1A:
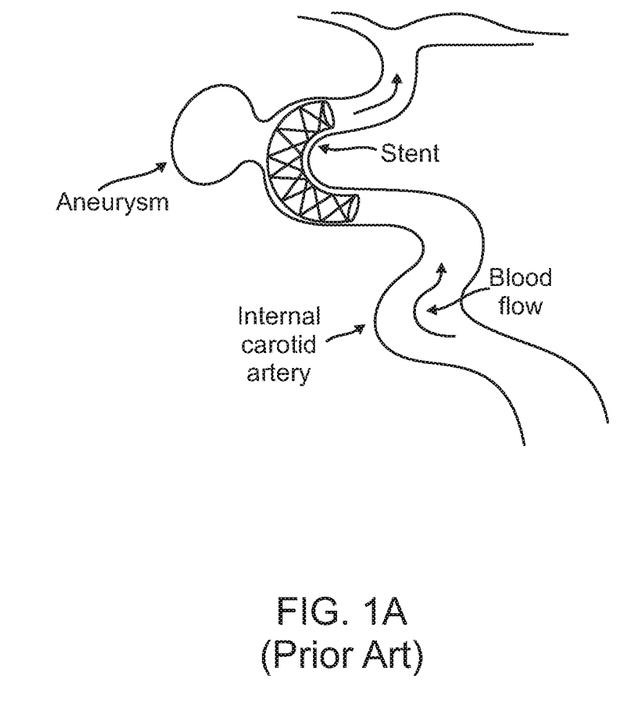
FIGS. 1A-1B illustrate use of a stent and an emboli coil for the treatment of an intracranial aneurysm.
Figure 1B:
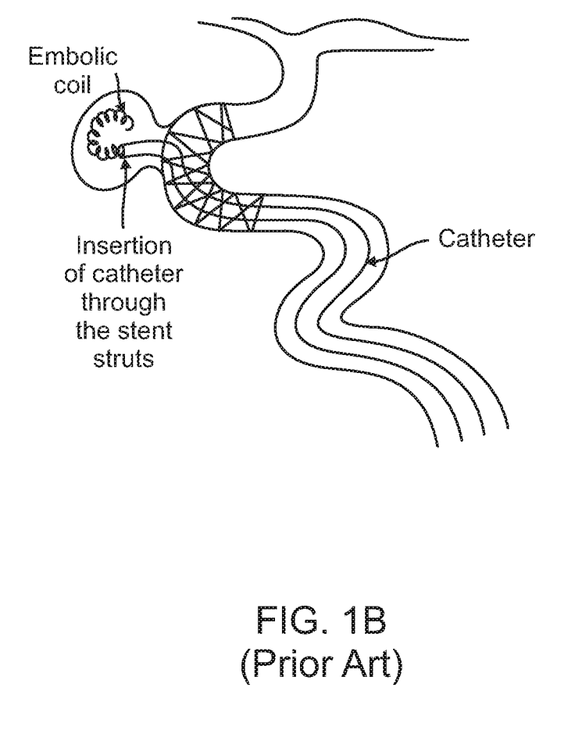

In coil embolization techniques using a combination of coils and a stent, the stent is used as a device that acts as a scaffolding structure to keep the coil inside the aneurysm volume, as shown in FIGS. 1A-B. After the stent is deployed covering the neck of the aneurysm, a delivery microcatheter is passed through a strut (also called an element) of the stent into the aneurysm dome and embolic coils are deployed through the catheter tip inside the aneurysm dome to fill the aneurysm volume.

A significant problem with coil embolization techniques is that during the process of filling the aneurysm volume, the coils or blood clots at the embolization site sometimes herniate into the parent artery if the stent fails to provide adequate scaffolding. Coils or blood clots herniating into the parent artery may escape from the aneurysm volume and travel downstream into the blood vessel and cause a stroke or other life threatening complications.

Another technique for treating aneurysms is with the use of a flow diverting stent. A flow diverter is placed in a blood vessel such that it spans the neck region of an aneurysm, thereby diverting blood flow away from the aneurysm sac. The stagnant blood inside the aneurysm sac may then clot and the aneurysm may heal.

Flow diverters, however, also suffer from complications. Braided devices used in the neurovasculature are bulky and often cannot access distal aneurysms. Use of these devices may also result in incomplete or delayed aneurysm occlusion, which can lead to delayed aneurysm rupture and stroke. In other vascular beds, such as the aorta or arteries of the lower extremities, covered stents are used to treat aneurysms. The most commonly used materials for covered stents include polytetrafluoroethylene (PTFE) and polyethylene terephthalate (PET). Both of these materials add substantial bulk, making the stent unsuitable for use in certain vascular beds, such as the neurovasculature. In addition, these materials tend to be impermeable or only semipermeable. This limits tissue in-growth into the stent covering and leaves a foreign body that is continuously exposed to blood. Because of this, there is a long-term risk of acute thrombosis and stenosis inside the stent. Moreover, because these stents are impermeable to blood flow they will cut-off blood flow to any vessels adjacent to the aneurysm that are covered with the stent. This can lead to ischemia of critical tissues such as the intestine. Further, blood clots formed at the covered stent implanted site may dislodge and cause a heart attack, stroke, or other life threatening complications.

A significant problem with stents, whether used to provide scaffolding to coils in coil embolization techniques or as a covered stent in flow diversion techniques, is their tendency to kink and failing to achieve good wall apposition when placed in torturous vascular beds. Accordingly, there is a need in the art for improved stents that are more kink resistant and achieve improved wall apposition, while simultaneously serving as a good scaffold for coil-based aneurysm treatment techniques.

SUMMARY

In one or more embodiments, a stent includes a first longitudinally extended cylinder having a C-shaped cross-section, the first cylinder including a plurality of first longitudinal struts and an array of first radial struts extending between the first longitudinal struts, and a second longitudinally extended cylinder having a C-shaped cross-section, the second cylinder including a plurality of second longitudinal struts and an array of second radial struts extending between the second longitudinal struts. The first cylinder and the second cylinder are configured to form a dense mesh when assembled.

In some embodiments, the first cylinder and the second cylinder are assembled, and a part of the first cylinder and a part of the second cylinder overlap to form the dense mesh. In some embodiments, more than half of the first cylinder and more than half of the second cylinder overlap to form the dense mesh.

In some embodiments, the second cylinder is disposed within the first cylinder. In some embodiments, the first cylinder and the second cylinder are aligned such that an opening of the first cylinder and an opening of the second cylinder are on opposing sides of the stent radially.

In some embodiments, the first cylinder and the second cylinder are attached at a joining location including a part of the first longitudinal struts and a part of the second longitudinal struts. In some embodiments, the first cylinder and the second cylinder are attached at the joining location by winding a tube or a coil around the part of the first longitudinal struts and the part of the second longitudinal struts.

In some embodiments, the first cylinder and the second cylinder are attached at the joining location further by a solder disposed within the wounded tube or coil. In some embodiments, the tube or coil includes a radiopaque marker.

In some embodiments, the first and second radial struts include straight struts, sinusoidal-shaped struts, or both. In some embodiments, the first and second longitudinal struts each include a central strut and two edge struts. In some embodiments, the first and second longitudinal struts include S-shaped struts that connect to and extend from a corresponding central strut towards a corresponding edge strut, curve around to extend towards the corresponding central strut, and curve around to extend to and connect to the corresponding edge strut. In some embodiments, a take-off angle of the first radial struts from a corresponding one of the first longitudinal struts is between 15° to 90°, and a take-off angle of the second radial struts from a corresponding one of the second longitudinal struts is between 15° to 90°. In some embodiments, the first cylinder and the second cylinder are same in shape.

In one or more embodiments, a stent includes a first longitudinally extended cylindrical-shaped member, the first member including a plurality of first longitudinal struts and an array of first radial struts extending between the first longitudinal struts. The stent includes an overlapping region to form a dense mesh.

In some embodiments, the overlapping region includes a part of the first member overlapping around another part of the first member. In some embodiments, the overlapping region includes more than half of an outer surface of the stent.

In some embodiments, the first member has a C-shaped cross-section, and the stent further includes a second longitudinally extended cylindrical-shaped member having a C-shaped cross-section, the second member including a plurality of second longitudinal struts and an array of second radial struts extending between the second longitudinal struts. The overlapping region is formed by overlapping at least a part of the first member and at least a part of the second member when assembled.

In some embodiments, the first member and the second member are assembled, and the second member is disposed within the first member. In some embodiments, the first member and the second member are aligned such that an opening of the first member and an opening of the second member are on opposing sides of the stent radially.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

By design, a stent is a cylindrical shape device that should be compactable so it can be delivered via a small delivery catheter and should be flexible so it can be tracked through tortuous blood vessels in the brain. A self-expandable stent is a type of stent that expands to the diameter of the blood vessel after it has been deployed from the delivery catheter. A self-expandable stent is made from a superelastic alloy such as an alloy of Nickel and Titanium, also called nitinol.

A self-expandable stent is made from a hypotube made with superelastic alloy material. The stent design is first drawn as a flat pattern (how a stent would look like if sliced longitudinally and pressed flat) on a Computer-Aided-Design (CAD) software. The same design pattern of the stent is then created on the hypotube by cutting it on to the hypotube using a powerful laser beam. After performing a series of post-processing work (which removes much of material from the laser-cut stent to soften) on the laser-cut part, a final stent device with its final specifications is produced. In order to deliver the stent device to its target location in the blood vessel, the stent must have a delivery system.

A stent delivery system can be a long wire with variable flexibility profile having some mechanism for attaching and detaching the stent. There are several mechanisms of detachment used in the market such as electrolytic detachment, twist-type detachment or mechanical detachment.

Figure 2:
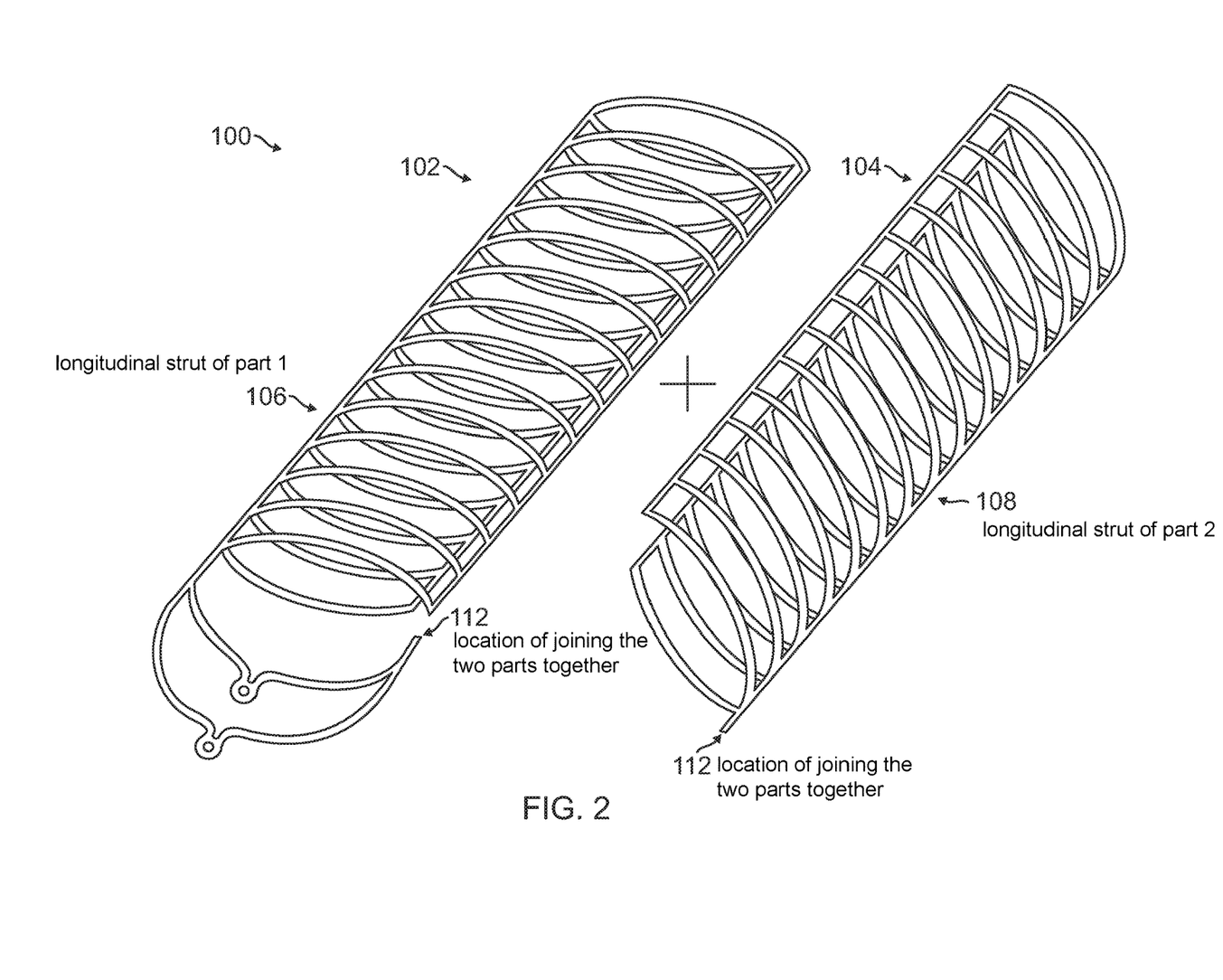
FIG. 2 is a diagrammatic perspective view of individual halves of a stent according to an embodiment.

A typical self-expandable stent is a one piece cylindrical device cut from a cylindrical hypotube of a superelastic alloy. In one or more embodiments, a stent 100 is constructed with two parts 102, 104, each part representing one half of the stent and the design of one part 102 being the mirror image of the other 104 as shown in FIG. 2. The first half 102 is also referred to as a first cylinder 102 or a first member 102, and the second half 104 is also referred to as a second cylinder 104 or a second member 104. The first half 102 and the second half 104 may be aligned and assembled such that the longitudinal strut 106 of the first half 102 and the longitudinal strut 108 of the second half 104 are on opposing sides of the stent 100, and the longitudinal opening of first half 102 and longitudinal opening of second half 104 are on opposing sides of the stent 100.

Figures 3A, 3B:
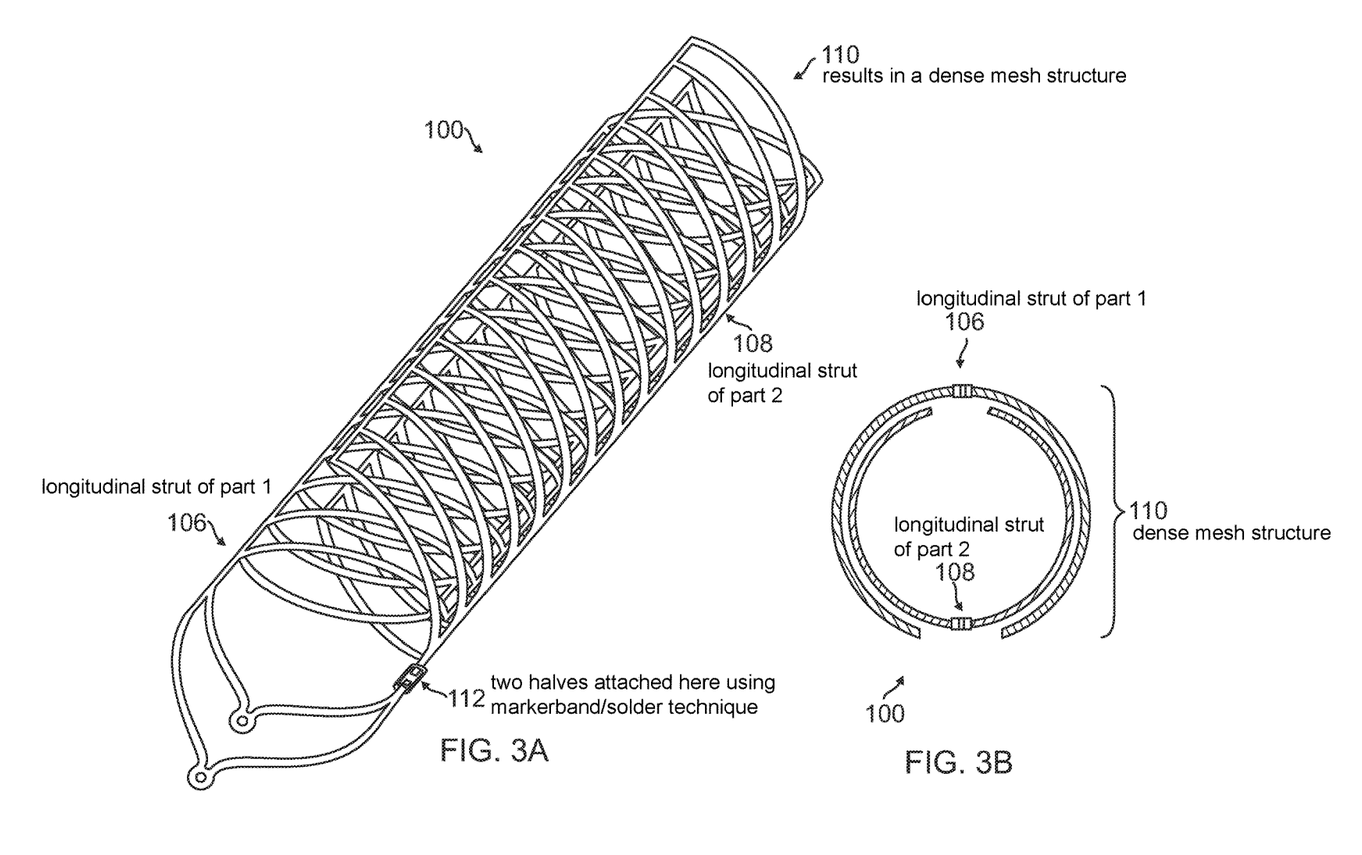
FIGS. 3A-3B are diagrammatic perspective views of the individual halves of the stent of FIG. 2 aligned before assembly.

After aligning the two parts 102, 104 together in the manner shown in FIGS. 3A-3B, the final assembled stent 100 results in a dense strut structure such as a dense mesh structure 110. The dense mesh structure 110 of the stent 100 provides the scaffold for the retention of the embolic coils. At the same time, since the struts are not weaved into each other, the struts have the agility to move and provide a passage if a catheter is to be passed through the mesh structure 110. To assemble the two parts 102, 104 together, the longitudinal struts 106, 108 are aligned and subsequently joined by using either soldering, marker band crimping, polymer heat shrinking or any other method with a biocompatible material at, for example, location 112.

Figures 4, 5:
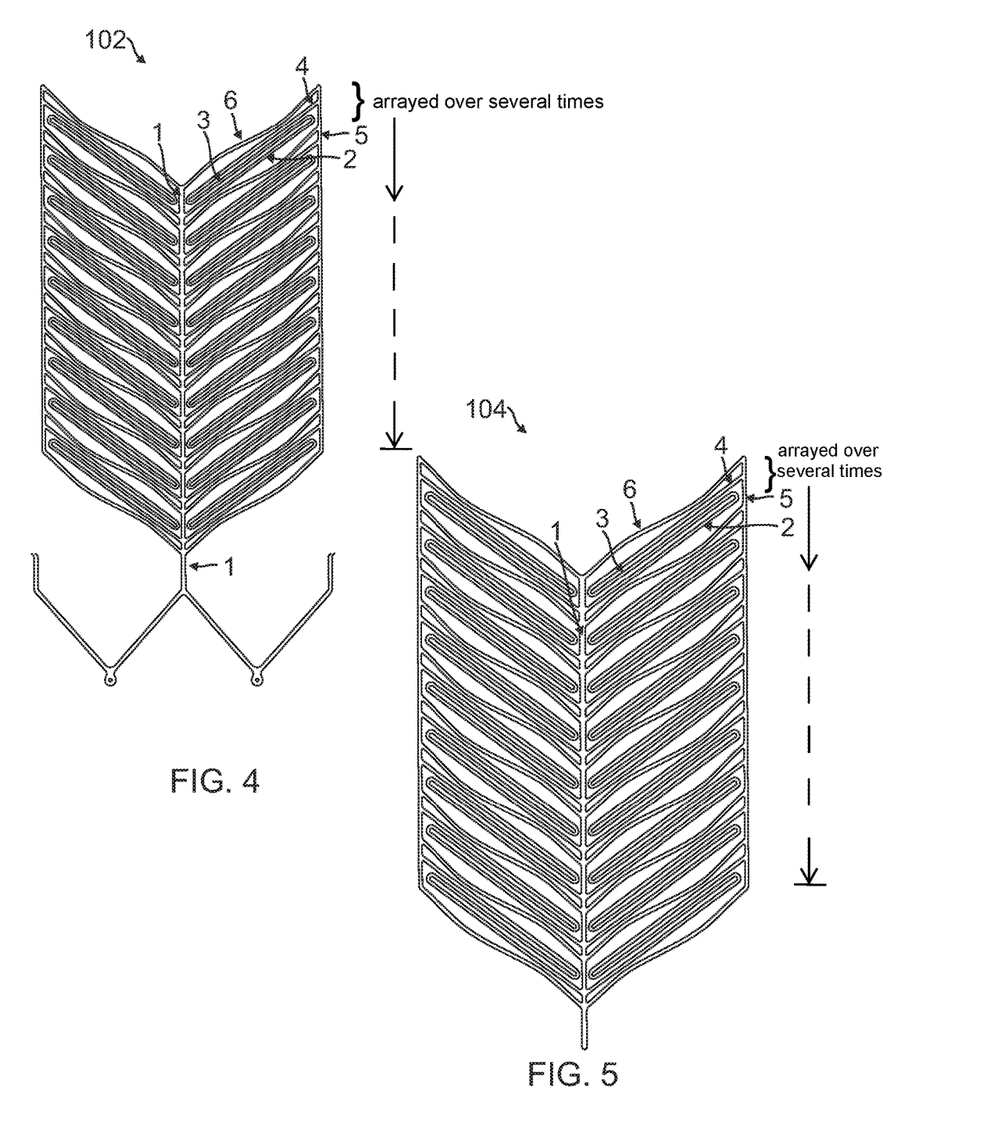
FIG. 4 is a diagrammatic flat pattern view of a first half of the stent of FIG. 2.
FIG. 5 is a diagrammatic flat pattern view of a second half of the stent of FIG. 2.

In one embodiment, the strut design of the first half 102 and the second half 104 may be as shown in FIG. 4 and FIG. 5, respectively. FIG. 4 and FIG. 5 show a complete design drawn as a flat pattern (representing how each half 102, 104 would look if pressed flat) in the CAD software. Each half 102, 104 consists of two different designs of radial struts (sinusoidal strut 6 and S-shaped strut 2-4) but arrayed multiple times along the length of the stent 100. One strut 6 runs directly from longitudinal strut 1 (such as longitudinal strut 106, 108), also referred to as a central strut 1, to a longitudinal strut 5, also referred to as an edge strut 5, at the other end. The strut 6 has a sinusoidal shape for enhanced flexibility. The other strut 2-4 includes struts 2, 3, and 4 and has an "S" shape as shown in FIG. 4. The "S" shaped strut originates from the longitudinal strut 1, transverses straight as strut 2 towards the other longitudinal strut 5 at which point it turns around and transverses the same length back as strut 3 in parallel to strut 2 and turns back one more time as strut 4 that runs parallel to strut 2 and 3 and finally connects to the other longitudinal strut 5. This S-shaped strut 2-4 adds to the overall flexibility of the device 100 and advantageously provides the desired kink resistance that a neurovascular stent is required to possess. These two struts (sinusoidal 6 and S-shaped 2-4) repeat themselves (array) multiple times for the remainder of length of the device 100.

Figure 6:
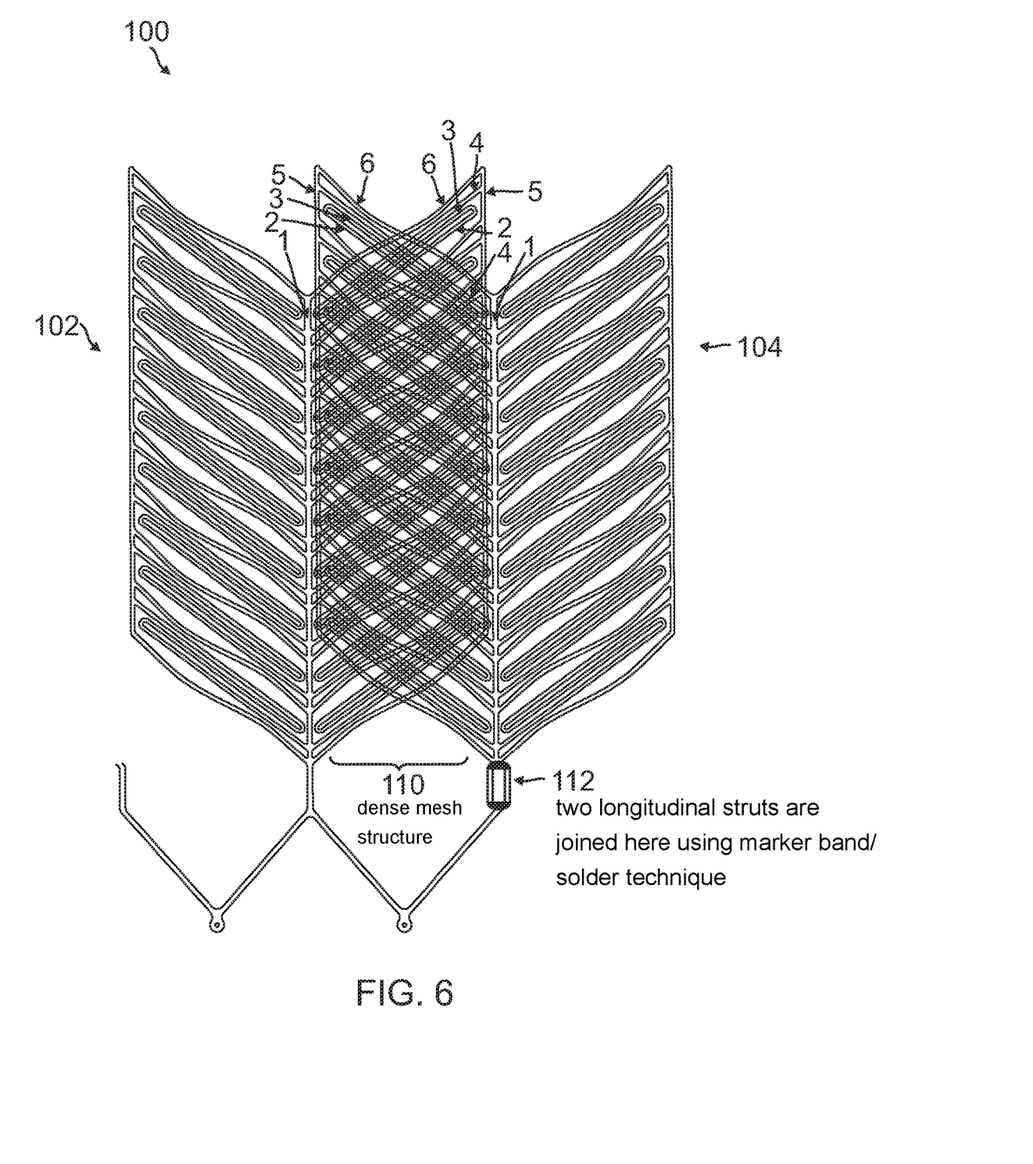
FIG. 6 is a diagrammatic flat pattern view showing the overlapping of the two halves of the stent of FIG. 2.

Due to the complexity associated with the 3-dimensional drawing of the stent 100 constructed of two halves 102, 104, the resulting strut structures of the final assembled stent 100 is illustrated by overlapping the two flat patterns (as if the stent has been flattened) of both parts 102, 104 on top of each other as shown in FIG. 6.

Figure 7A:
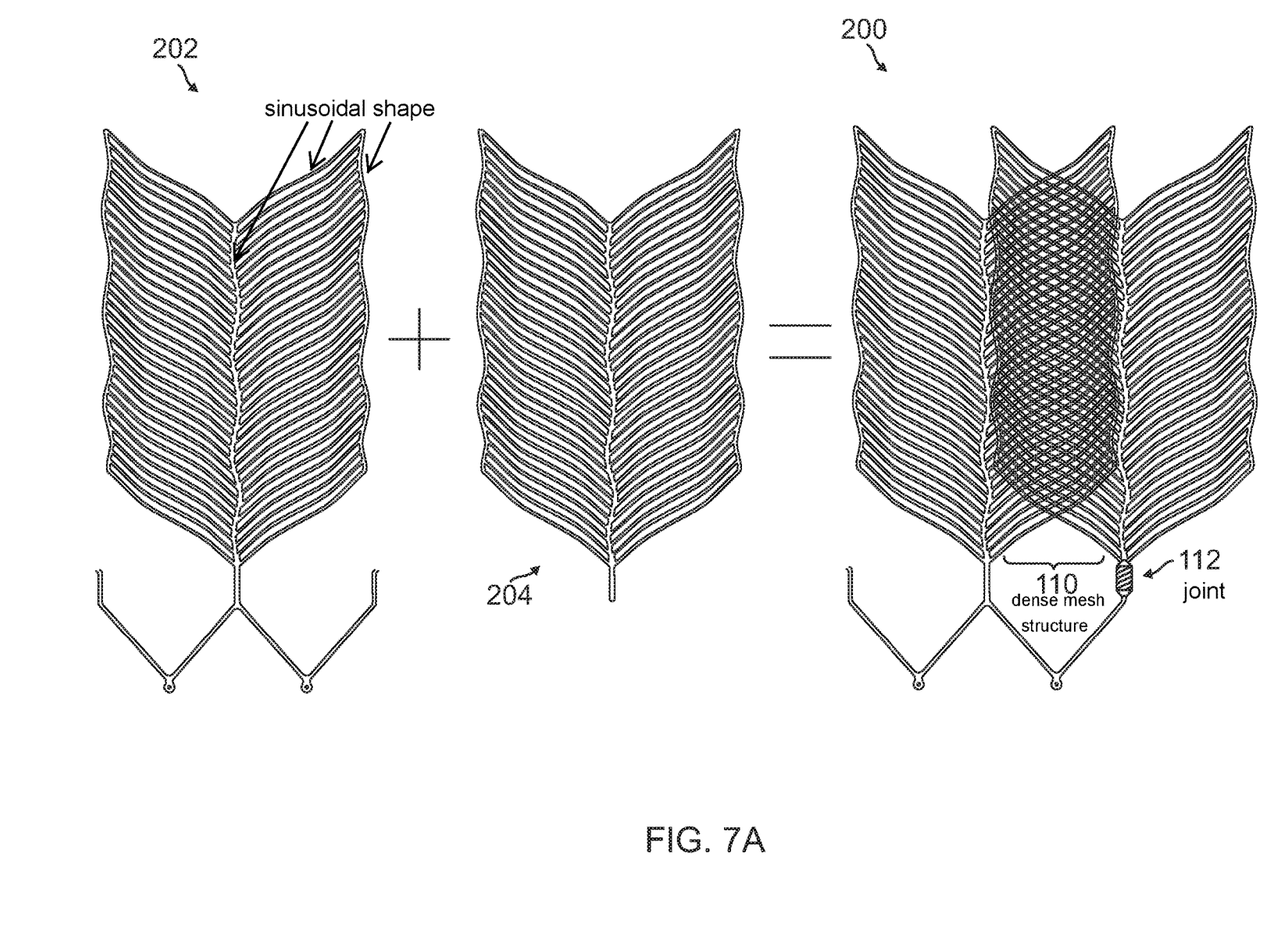
FIG. 7A is a diagrammatic flat pattern view of a stent having sinusoidal struts according to an embodiment.
Figure 7B:
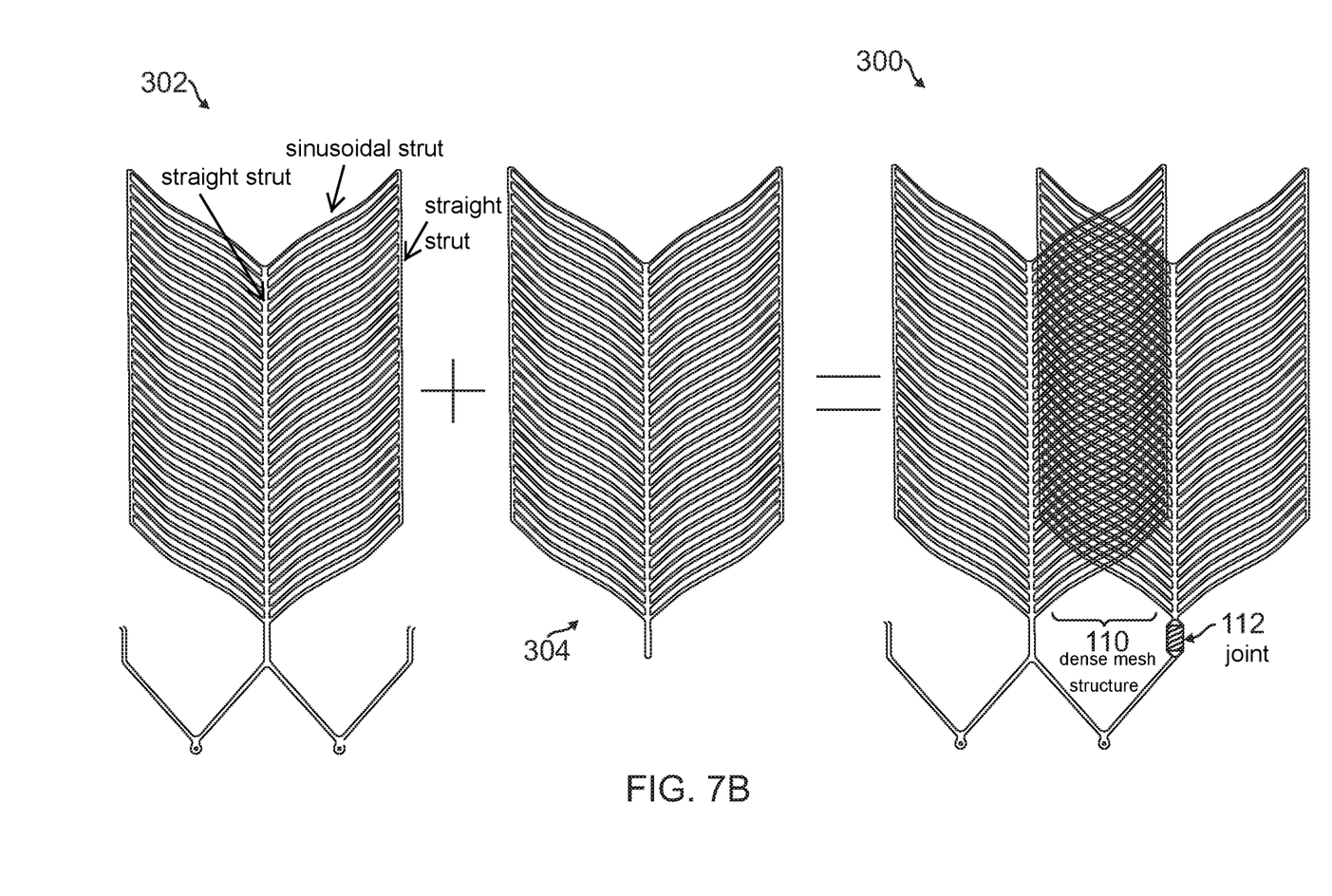
FIG. 7B is a diagrammatic flat pattern view of a stent having straight longitudinal struts and sinusoidal radial struts according to an embodiment.
Figure 7C:
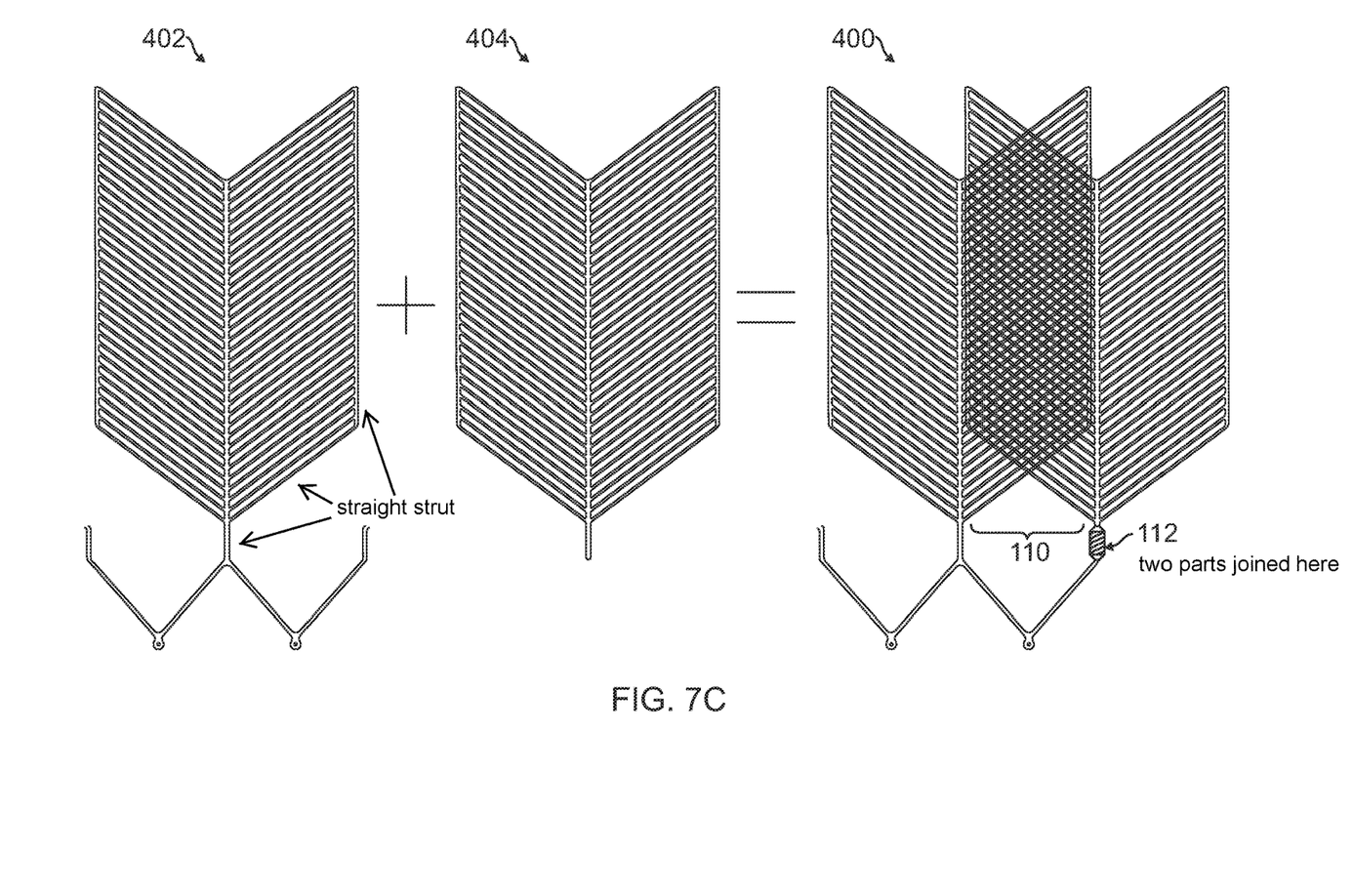
FIG. 7C is a diagrammatic flat pattern view of a stent having straight struts according to an embodiment.

In other embodiments, the stent 100 can be constructed with struts of various geometries. Examples of few such variations are shown in FIG. 7A-C. In one embodiment, a stent 200 includes a first half 202 and a second half 204 having sinusoidal longitudinal struts and sinusoidal radial struts as shown by the flat pattern view in FIG. 7A. In another embodiment, a stent 300 includes a first half 302 and a second half 304 having straight longitudinal struts and sinusoidal radial struts as shown by the flat pattern view in FIG. 7B. In a further embodiment, a stent 400 including a first half 402 and a second half 404 having straight longitudinal struts and straight radial struts as shown by the flat pattern view in FIG. 7C.

Figure 8:
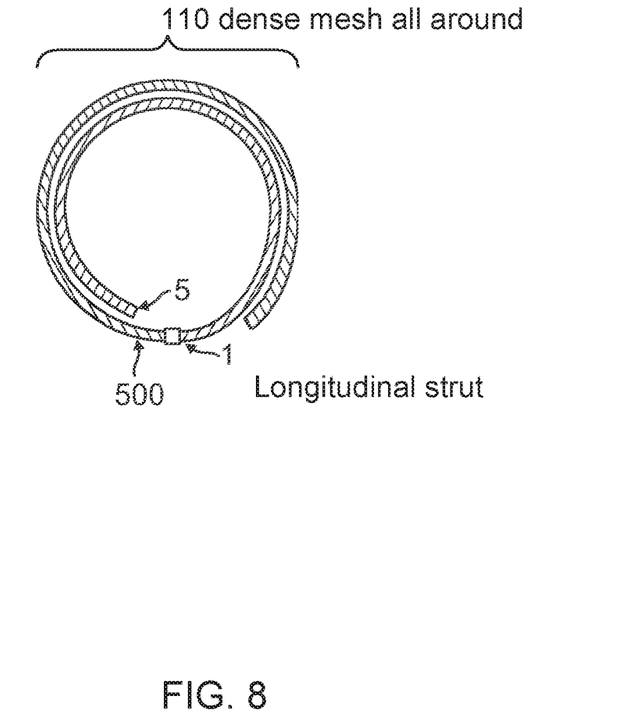
FIG. 8 is a diagrammatic cross-sectional view of a stent according to an embodiment.

In another embodiment, the stent 100 can be constructed using only one half (instead of two halves 102, 104 as above). An example of such stent 500 using only one half is shown in FIG. 8. In this configuration of the stent 500, the longitudinal struts 5 slide over each other as the stent is compressed in radial direction to a smaller diameter thereby resulting in a dense mesh structure 110 as shown in FIG. 8. In order to make this embodiment of stent 500 feasible inside a typical blood vessel, the length of the struts should be as long as possible.

Figure 9:
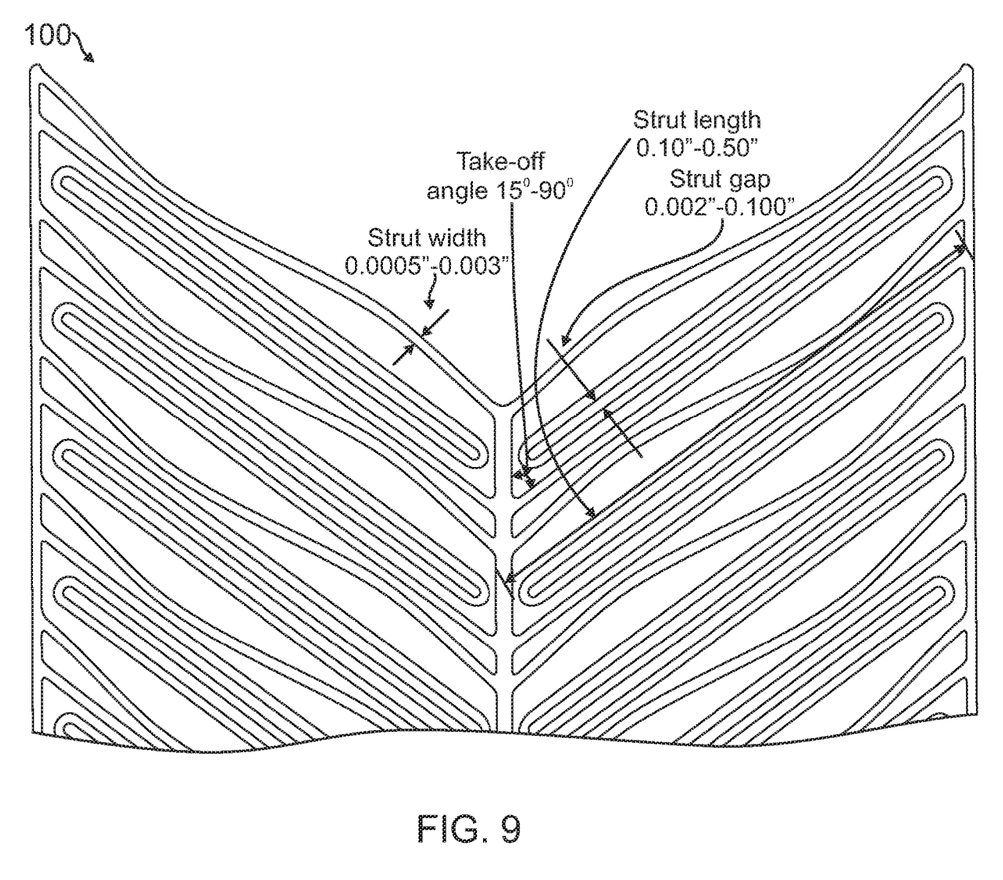
FIG. 9 is a diagrammatic flat-pattern view of a part of a stent illustrating exemplary dimensions according to an embodiment.

FIG. 9 shows a flat pattern view of a part of a stent device such as stent 100 and illustrates exemplary dimensions of stent 100 (e.g., implemented according to any of the examples shown in FIGS. 2-8). The dimensions of struts of a final assembled stent 100 can be anywhere from 0.0005" to 0.003" in width depending upon the degree of flexibility desired. The gap between the radial struts can be anywhere from 0.002" to 0.100" depending upon the degree of denseness desired. The take-off angle of the radial struts from the longitudinal strut can be anywhere from 15° to 90° as shown in FIG. 9. The length of the radial strut can be anywhere from 0.10" to 0.50" but not limited to this range. The length of the stent 100 can be anywhere from 10 mm to 60 mm. However a construction of a stent 100 of length beyond this range is entirely feasible. The diameter of the stent 100 can be anywhere from 2 mm to 7 mm. However, this method of construction is scalable for the diameters greater than 7 mm.

To construct this stent 100, first the flat patterns of each halves 102, 1074 of the stent 100 are drawn using a CAD software, for example AutoCAD. The strut width in the flat pattern can be anywhere between 0.0030" to 0.0050". The specification of the strut width depends upon the wall thickness of the nickel-titanium hypotube that the stent 100 is cut from. The electronic flat patterns are then programmed into a computerized laser-cutting equipment. After the equipment has been programmed, it drives a powerful laser beam along the edges of the design pattern and thereby cuts the exact same pattern from the nickel-titanium hypotube. The laser-cut stent 100 goes through a sequence of subsequent processes. Some of those include: stress-relief heat treatment at 500° C. to remove stresses from the laser-cut parts, microblasting to remove the outside oxide layer, expansion to a larger diameter by shape setting at 500° C., chemical etching and electro-polishing to remove much of material to obtain the final strut width.

The overlapping of nitinol stents 100 to get a dense mesh has been demonstrated before but only by deploying two finished stents separately, second stent inside the first one. The process of stenting an aneurysm in two separate deployments not only increases the clinical risks associated with the deployment but also requires the catheter access through the first deployed stent.

One or more embodiments of the present disclosure facilitate the features of two overlapped-stents in one stent. Advantageous features of one or more embodiments of the present disclosure are the process of assembling the stent 100 using two parts 102, 104 and the process of joining the two parts together at a location such as location 112 as described herein. The stent 100 described in one or more embodiments of the present disclosure facilitate a dense mesh across the neck of an aneurysm using only a single deployment hence reducing the clinical risk. Since there is no second deployment involved with this stent 100, it eliminates the requirement of catheter access through the deployed stent.

Figures 10A, 10B:
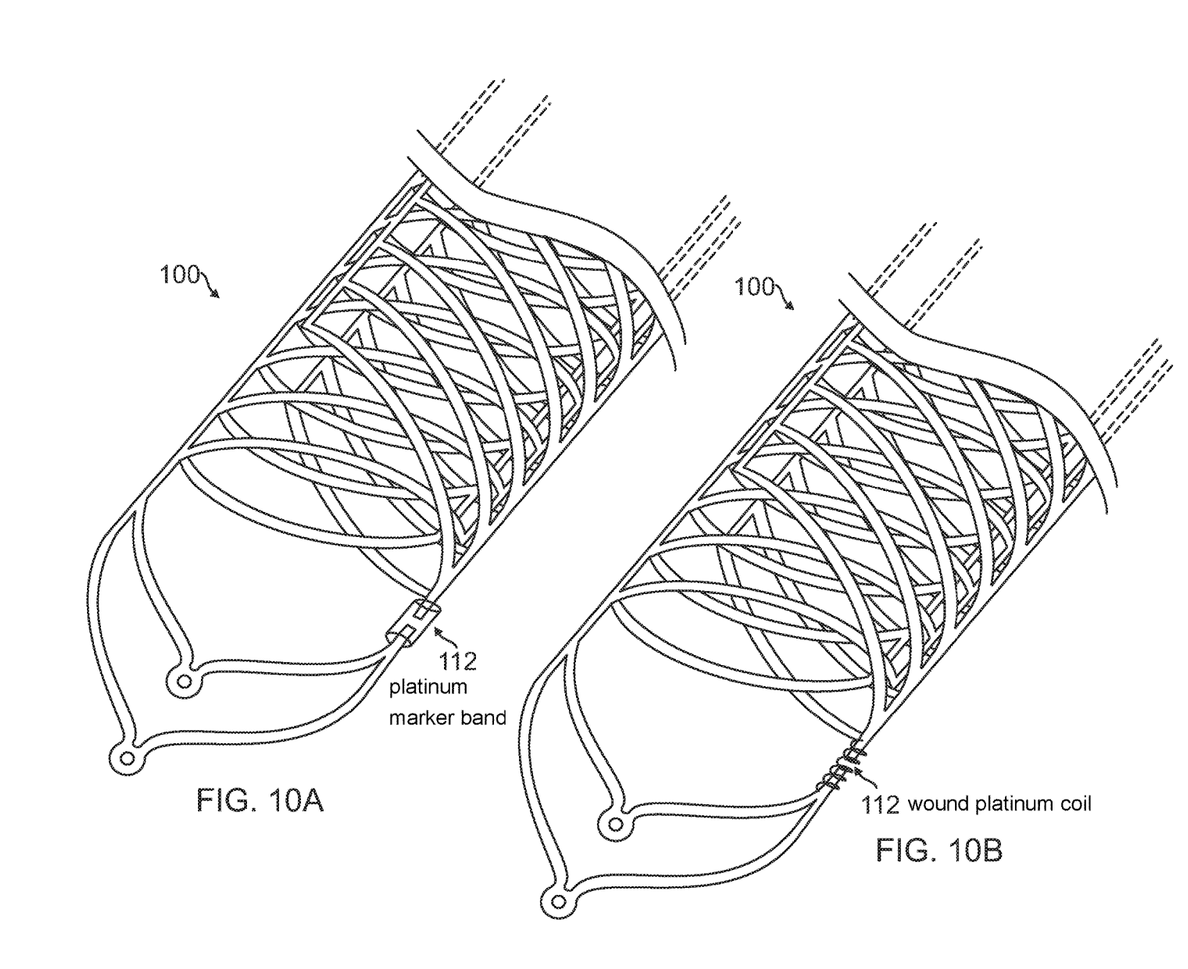
FIG. 10A is a diagrammatic perspective view of a part of a stent with a tube joining two halves of the stent according to an embodiment.
FIG. 10B is a diagrammatic perspective view of a part of a stent with a wounded coil joining two halves of the stent according to an embodiment.
Figure 11A:
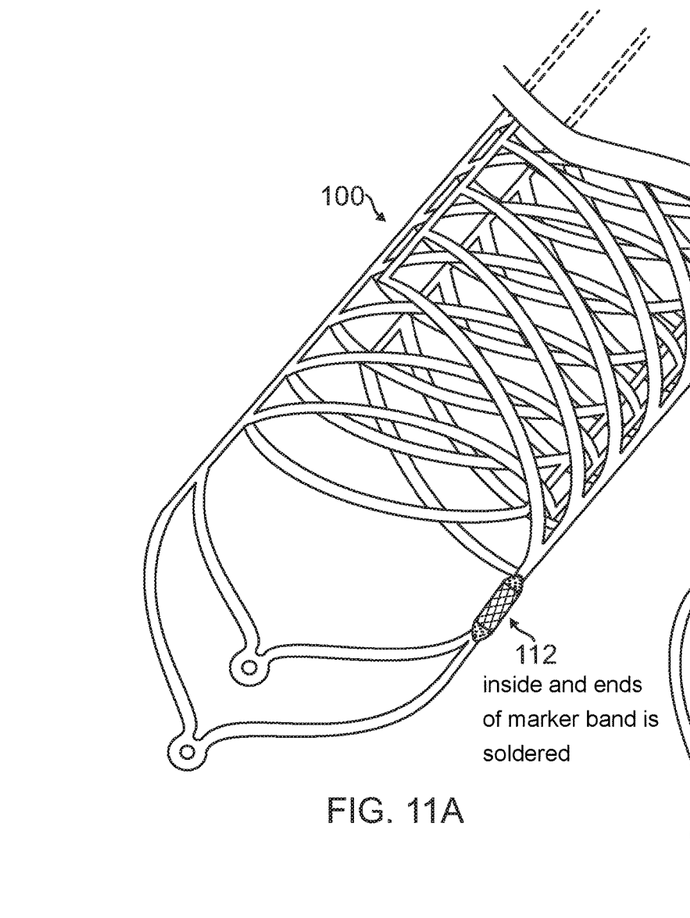
FIG. 11A is a diagrammatic perspective view of a part of a stent with a soldered tube according to an embodiment.
Figure 11B:
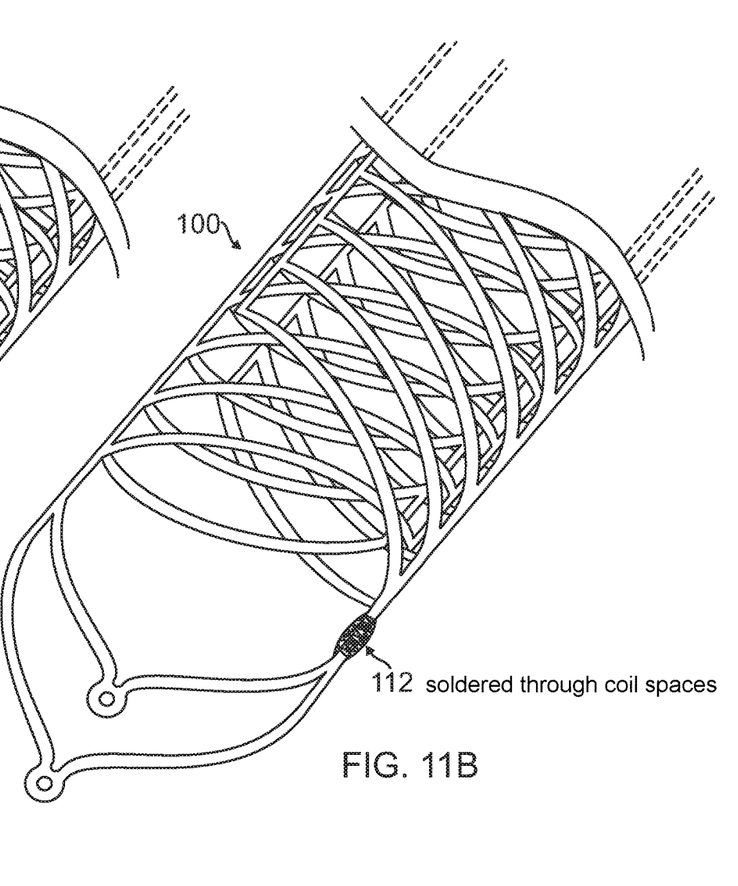
FIG. 11B is a diagrammatic perspective view of a part of a stent with a soldered wounded coil according to an embodiment.
Figure 12:
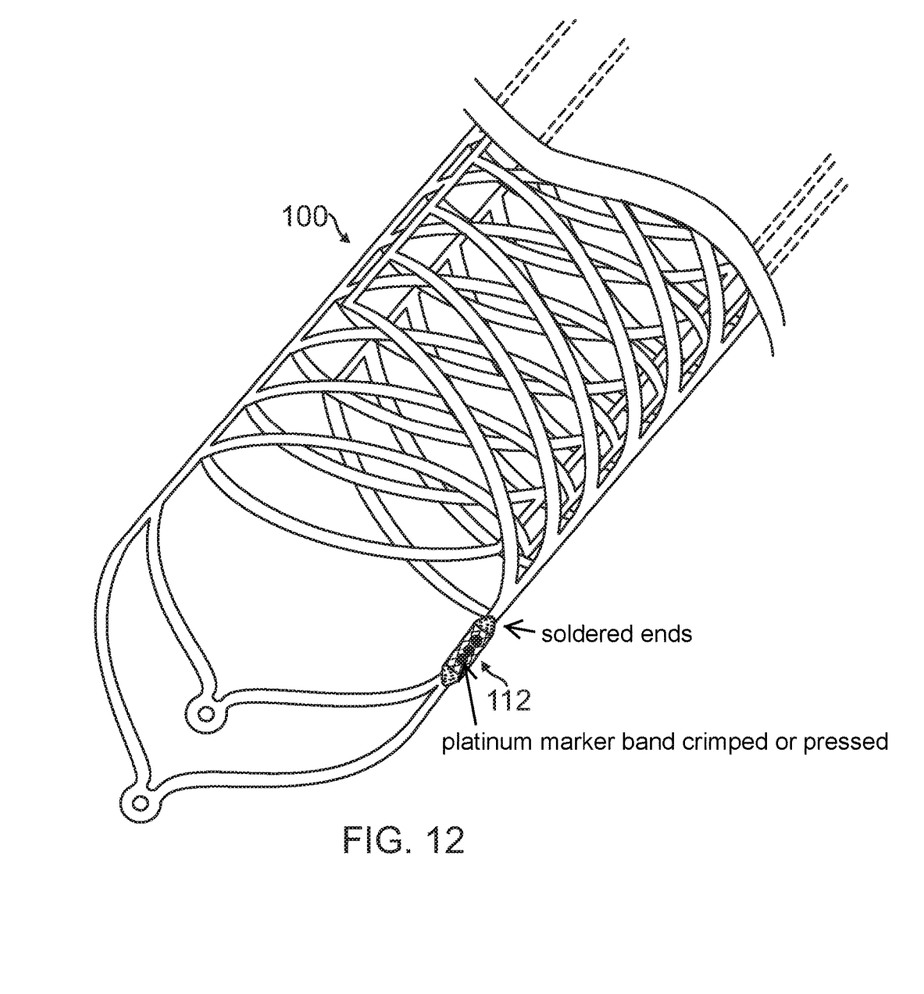
FIG. 12 is a diagrammatic perspective view of a part of a stent with a crimped tube according to an embodiment.

In one embodiment of a process of joining the two parts 102, 104, the longitudinal struts of the respective parts are aligned and wrapped (e.g., using a radiopaque marker) that could be in the form of a tube such as a platinum marker band as shown in FIG. 10A or a wound coil such as a platinum coil as shown in FIG. 10B. After the process of wrapping the struts, the remaining space inside the tube or coil may be filled with a solder to enforce the joining of the two struts as shown in FIGS. 11A-B. In some embodiments, a tube such as a platinum marker band may be mechanically crimped prior to filling the inside of the space with the solder as shown in FIG. 12. Alternatively, the tube may be crimped and a solder may not be applied, or the filling of the space with the solder may be performed prior to crimping the tube.

In the final set of processes, additional radiopaque markers (platinum or gold material) may be added at desired locations of the stent 100 using the method of crimping or soldering. In the final assembly the stent is then mounted on a delivery system and loaded inside an introducer sheath.

Advantageously, since the two parts 102, 104 of an assembled stent 100 are free to slide inside one another, the stent 100 exhibits excellent resistance to kinking when deployed inside a tight curve. Another advantageous feature of one or more embodiments of the present disclosure is the ease of manufacturability of the stent 100.

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. A stent comprising:
a first longitudinally extended cylinder having a C-shaped cross-section, the first cylinder comprising a plurality of first longitudinal struts and an array of first radial struts extending between the first longitudinal struts; and
a second longitudinally extended cylinder having a C-shaped cross-section, the second cylinder comprising a plurality of second longitudinal struts and an array of second radial struts extending between the second longitudinal struts;
wherein the first cylinder and the second cylinder are configured to form a dense mesh when assembled, and
wherein the first and second longitudinally extended cylinders further comprise S-shaped struts that connect to and extend from a corresponding longitudinal central strut towards a corresponding longitudinal edge strut, curve around to extend towards the corresponding central strut, and curve around to extend to and connect to the corresponding edge strut.

2. The stent of claim 1, wherein the first cylinder and the second cylinder are assembled, and wherein a part of the first cylinder and a part of the second cylinder overlap to form the dense mesh.

3. The stent of claim 2, wherein more than half of the first cylinder and more than half of the second cylinder overlap to form the dense mesh.

4. The stent of claim 2, wherein the second cylinder is disposed within the first cylinder.

5. The stent of claim 2, wherein the first cylinder and the second cylinder are aligned such that an opening of the first cylinder and an opening of the second cylinder are on opposing sides of the stent radially.

6. The stent of claim 2, wherein the first cylinder and the second cylinder are attached at a joining location comprising a part of the first longitudinal struts and a part of the second longitudinal struts.

7. The stent of claim 6, wherein the first cylinder and the second cylinder are attached at the joining location by winding a tube or a coil around the part of the first longitudinal struts and the part of the second longitudinal struts.

8. The stent of claim 6, wherein the first cylinder and the second cylinder are attached at the joining location by winding a tube around the part of the first longitudinal struts and the part of the second longitudinal struts, and
wherein the first cylinder and the second cylinder are attached at the joining location further by a solder disposed within the wounded tube.

9. The stent of claim 8, wherein the tube comprises a radiopaque marker.

10. The stent of claim 1, wherein the first and second radial struts comprise sinusoidal-shaped struts.

11. The stent of claim 1, wherein a take-off angle of the first radial struts from a corresponding one of the first longitudinal struts is between 15° to 90°, and wherein a take-off angle of the second radial struts from a corresponding one of the second longitudinal struts is between 15° to 90°.

12. The stent of claim 1, wherein the first cylinder and the second cylinder are same in shape.

* * * * *